United States Patent [19]

Mark

[11] Patent Number: 4,609,501
[45] Date of Patent: Sep. 2, 1986

[54] PROCESS FOR THE PREPARATION OF AROMATIC CARBONATES

[75] Inventor: Victor Mark, Evansville, Ind.

[73] Assignee: General Electric Company, Mt. Vernon, Ind.

[21] Appl. No.: 565,895

[22] Filed: Dec. 27, 1983

[51] Int. Cl.⁴ .............................................. C07C 68/06
[52] U.S. Cl. ..................................................... 260/463
[58] Field of Search ........................................ 260/463

[56] References Cited

U.S. PATENT DOCUMENTS

| | | | |
|---|---|---|---|
| 3,255,236 | 6/1966 | Selwitz et al. | 560/92 |
| 3,767,648 | 10/1973 | Fujita et al. | 260/239.3 A |
| 3,808,245 | 4/1974 | O'Connor et al. | 260/410.7 |
| 4,045,464 | 8/1977 | Romano et al. | 260/463 |
| 4,112,235 | 9/1978 | Schmerling et al. | 560/1 |
| 4,182,726 | 1/1980 | Illuminati et al. | 260/463 |
| 4,410,464 | 10/1983 | Hallgren | 260/463 |

FOREIGN PATENT DOCUMENTS 2286157 9/1975 France .

OTHER PUBLICATIONS

*Chemical Abstracts,* vol. 57: 9981d, "Identification of Carboxylic Acids in Alkyd and Polyester Coating Resins".
*Chemical Abstracts,* vol. 61: 4223f, "Acrylic Acid Esters", Sims and Southwood.

*Primary Examiner*—Donald G. Daus
*Assistant Examiner*—Stephen M. Kapner
*Attorney, Agent, or Firm*—Myron B. Kapustij; Martin B. Barancik

[57] ABSTRACT

An improved process for the preparation of aromatic carbonates selected from aliphatic aromatic carbonates and diaromatic carbonates comprising reacting at least one phenolic compound with at least one dialiphatic carbonate or at least one aliphatic aromatic carbonate in the presence of a catalytic amount of a catalyst comprised of (i) at least one Lewis acid, and (ii) at least one protic acid.

10 Claims, No Drawings

PROCESS FOR THE PREPARATION OF AROMATIC CARBONATES

BACKGROUND OF THE INVENTION

Organic carbonates such as the dialiphatic carbonates, aliphatic aromatic carbonates, and diaromatic carbonates are generally conventionally prepared by the reaction of phenols or alcohols with phosgene in the presence of acid binding agents such as the organic bases or inorganic bases. However, due to the toxicity of phosgene it is sometimes desirable to avoid the use of phosgene in the preparation of these organic carbonates.

Since the dialiphatic carbonates, such as the dialkyl carbonates, may be prepared from alcohols by routes other than those utilizing phosgene, i.e, catalytically from carbon monoxide and oxygen, it is possible to prepare the aliphatic aromatic carbonates and the diaromatic carbonates from these dialiphatic carbonates and phenols without using phosgene. Such phosgene free processes are disclosed in U.S. Pat. Nos. 4,045,464 and 4,182,726. These patents disclose the prepartion of alkyl aryl carbonates and diaryl carbonates from dialkyl carbonates and phenols in the presence of a catalyst which is selected from Lewis acids and compounds of transition metals.

It would, however, be most advantageous if a phosgene free process which is more effective and efficient than those presently available could be provided for the preparation of aliphatic aromatic carbonates and diaromatic carbonates from dialiphatic carbonates. It is, therefore, an object of the instant invention to provide such a phosgene free transesterification process for the production of aliphatic aromatic carbonates and diaromatic carbonates from dialiphatic carbonates.

SUMMARY OF THE INVENTION

The instant invention is directed to a transesterification process for the preparation of aliphatic aromatic carbonates and diaromatic carbonates from dialiphatic carbonates utilizing a catalytic amount of a catalyst system which is comprised of, in physical admixture:
(i) at least one Lewis acid; and
(ii) at least one protic acid.

DESCRIPTION OF THE INVENTION

The instant invention is directed to an improved transesterification process for the preparation of aromatic carbonates from aliphatic carbonates, the improvement comprising carrying out the reaction in the presence of a catalytic amount of a catalyst which is comprised of a physical admixture of (i) at least one Lewis acid, and (ii) at least one protic acid.

The aromatic carbonates which may be prepared by the process of the instant invention include the aliphatic aromatic carbonates and the diaromatic carbonates. The aliphatic aromatic carbonates may be represented by the general formula

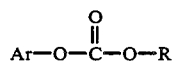

I.

wherein:
R is selected from monovalent aliphatic hydrocarbon radicals; and

Ar is selected from monovalent aromatic radicals.

The preferred monovalent aliphatic hydrocarbon radicals represented by R are the alkyl radicals and the cycloalkyl radicals. The preferred alkyl radicals are those containing from 1 to about 12 carbon atoms. These alkyl radicals include the straight chain alkyl radicals and the branched alkyl radicals. Some illustrative non-limiting examples of these alkyl radicals include methyl, ethyl, propyl, isopropyl, butyl, isobutyl, pentyl, neopentyl, hexyl, and heptyl. The preferred cycloalkyl radicals are those containing from 4 to about 7 ring carbon atoms. Some illustrative non-limiting examples of these cycloalkyl radicals include cyclobutyl, cyclopentyl, methylcyclohexyl, cyclohexyl, and cycloheptyl.

The monovalent aromatic radicals represented by Ar include the aryl radicals containing from 6 to 12 carbon atoms. These include phenyl, naphthyl, and biphenyl. Preferred aryl radicals are those represented by the general formula

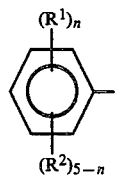

wherein:
$R^1$ is independently selected from monovalent hydrocarbon radicals and halogen radicals;
$R^2$ is hydrogen; and
n is a positive integer having a value of from 0 to 5 inclusive.

The monovalent hydrocarbon radicals represented by $R^1$ include the alkyl radicals, cycloalkyl radicals, aryl radicals, aralkyl radicals, and alkaryl radicals.

The preferred alkyl radicals represented by $R^1$ are those containing from 1 to about 10 carbon atoms. These include the straight chain and branched alkyl radicals. The preferred cycloalkyl radicals represented by $R^1$ are those containing from 4 to about 7 ring carbon atoms. The preferred aryl radicals are those containing from 6 to 12 ring carbon atoms and include phenyl, biphenyl and naphthyl. The preferred aralkyl and alkaryl radicals represented by $R^1$ are those containing from 7 to about 14 carbon atoms.

The preferred halogen radicals represented by $R^1$ are chlorine and bromine.

The diaromatic carbonates may be represented by the general formula

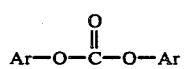

II.

wherein Ar is as defined hereinafore.

The aliphatic aromatic carbonates of the instant invention may be prepared by the reaction of a phenol of the general formula

wherein Ar is as defined hereinafore, with a dialiphatic carbonate of the general formula

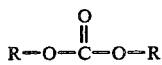

wherein R is as defined hereinafore, in the presence of a catalytic amount of the catalyst of the instant invention.

The reaction of the phenol with the dialiphatic carbonate may be represented by the formula

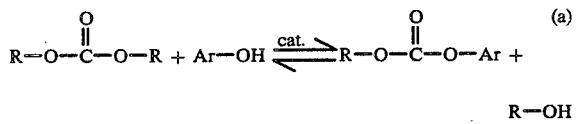

(a)

wherein R and Ar are as defined hereinafore and cat. is a catalytic amount of the catalyst of the instant invention.

The diaromatic carbonates of the instant invention may be prepared by either one of two methods. The first method involves reacting the aliphatic aromatic carbonate formed as described hereinafore with a phenol, in the presence of a catalytic amount of the catalyst of the instant invention. This reaction may be represented by the general formula

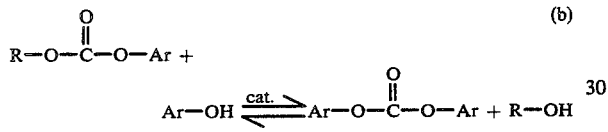

(b)

wherein R, Ar and cat. are as defined hereinafore.

The second method involves the reaction of the aliphatic aromatic carbonate with itself or with another aliphatic aromatic carbonate in the presence of a catalytic amount of the catalyst of the instant invention. This reaction may be represented by the general formula

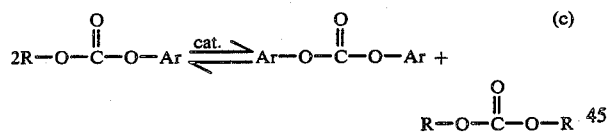

(c)

wherein Ar, R and cat. are as defined hereinafore.

The reactions depicted by formulae (a), (b) and (c) may be carried out in the liquid phase, with or without the presence of a solvent, at temperatures of from about 60° C. to about 300° C., preferably from about 150° C. to about 250° C. These reactions may be carried out at pressures ranging from subatmospheric pressures to superatmospheric pressures, e.g. from about 0.1 to about 50 atmospheres. These reactions proceed readily at atmospheric pressures.

Since the reactions depicted in Formulae (a) and (b) are equilibrium reactions, it is advantageous to remove the alcohol formed so as to continuously shift the equilibrium until the reactions reach completion. Since the alcohol is most conveniently removed by distillation it is desirable that the reactants in the equations depicted by Formulae (a) and (b) are so selected that the R—OH byproduct has a lower boiling point than the Ar—OH reactant and thus can be distilled off as it is formed. It is for this reason that the lower dialiphatic carbonates or aliphatic aromatic carbonates are the preferred reactants in the processes of the instant invention, i.e., R is a lower alkyl radical containing from 1 to about 4 carbon atoms in the aliphatic aromatic carbonates of Formula I and in the dialiphatic carbonates described hereinafore.

The preparation of the diaromatic carbonates by the reaction depicted by Formula (c) may also be conveniently achieved by the distillation of the dialiphatic carbonate coproduct. For this reason, it is also preferred that the aliphatic aromatic carbonate reactant be a lower aliphatic aromatic carbonate so that the dialiphatic carbonate coproduct may be readily distilled off, i.e., R in the aliphatic aromatic carbonate is a lower alkyl radical containing from 1 to about 4 carbon atoms.

In the preparation of the diaromatic carbonates of the instant invention it is preferred that the reaction process be continuous and be carried out in the same reaction vessel. That is to say, once the aliphatic aromatic carbonate is formed by the reaction of the dialiphatic carbonate and the phenol it is not removed from the reaction vessel but is allowed to further react with the phenol in the same reaction vessel to form the diaromatic carbonate.

While theoretically it requires two moles of phenol for every mole of dialiphatic carbonate to produce the diaromatic carbonate, in practice it is generally preferred to use an excess of the phenol reactant. Thus, for example, it is generally preferred to use an excess of phenol when reacting the dialiphatic carbonate with the phenol to produce the aliphatic aromatic carbonate, and it is also preferred to utilize an excess of phenol when reacting the phenol with the aliphatic aromatic carbonate to produce the diaromatic carbonate. Since it is generally preferred to employ a continuous process for the preparation of the diaromatic carbonates, it is preferred to use more than two moles of phenol for every mole of dialiphatic carbonate reactant utilized.

The amount of the catalyst of the instant invention utilized in the exchange reactions described herein is a catalytic amount. By catalytic amount is meant an amount effective to catalyze the transesterification reaction for the preparation of the aliphatic aromatic carbonates from the dialiphatic carbonates and the phenols or the diaromatic carbonates from the aliphatic aromatic carbonates and phenols. Generally this amount is in the range of from about 0.01 to about 25 weight percent, based on the amounts of dialiphatic carbonate or aliphatic aromatic carbonate reactants utilized, and preferably from about 0.1 to about 20 weight percent.

The catalysts of the instant invention are comprised of a physical mixture of (i) at least one Lewis acid, and (ii) at least one protic acid.

The Lewis acids are well known to those skilled in the art. Basically, according to standard and accepted definition of a Lewis acid, it is a substance that can take up an electron pair to form a covalent bond. Thus, a Lewis acid is an electron pair acceptor. Some illustrative non-limiting examples of Lewis acids include $BX_3$, $AlX_3$, $TiX_3$, $SnX_4$, $UX_4$, $TiX_4$, $VOX_3$, $VX_5$, $ZnX_2$, and $FeX_3$, wherein X is halogen, acetoxy, alkoxy, or aryloxy.

Protic acids are well known to those skilled in the art. Basically, according to the standard and accepted definition of a protic acid it is a substance which gives up a proton, i.e., it is a proton donor. More specifically, it is a substance which contains hydrogen which hydrogen under appropriate conditions forms hydrogen ions, $H^+$, or protons. The protic acids include the inorganic protic acids and the organic protic acids. Particularly useful organic protic acids are the organic sulfonic acids. Some illustrative non-limiting examples of protic acids include HCl, $H_2SO_4$, $H_3PO_4$, $H_2CO_3$, methanesulfonic acid, trifluoromethane sulfonic acid, benzene sulfonic acid, methane phosphonic acid, and HBr.

The mixture of the Lewis acid and the protic acid which forms the catalyst system of the instant invention contains an amount of protic acid effective to enhance or improve the catalytic activity of said mixture. Generally, this mixture contains a weight ratio of Lewis acid to protic acid of from about 20:1 to about 1:5.

It is further contemplated that the instant catalyst system comprised of a physical mixture of at least one Lewis acid and at least one protic acid would be effective in catalyzing any transesterification reaction. Thus, while the instant disclosure and examples are directed to the formation of aliphatic aromatic carbonates and diaromatic carbonates from dialiphatic carbonates and aliphatic aromatic carbonates, respectively, it is contemplated that this catalyst system would be effective in the formation of other esters via a transesterification process.

The instant catalyst system contains a physical mixture of at least one Lewis acid and at least one protic acid. Thus, for example, the instant system may contain only one Lewis acid admixed with one protic acid; two different Lewis acids admixed with one protic acid: two different protic acids admixed with one Lewis acid; or two or more different Lewis acids admixed with two or more different protic acids.

DESCRIPTION OF THE PREFERRED EMBODIMENT

In order to more fully and clearly illustrate the present invention the following examples are set forth. It is intended that the examples be considered as illustrative rather than limiting the invention as disclosed and claimed herein. In the examples all parts and percentages are on a weight basis, unless otherwise indicated.

The following examples illustrate the preparation of aliphatic aromatic (alkyl aryl) carbonates and diaromatic (diaryl) carbonates from dialiphatic (dialkyl) carbonates utilizing only a Lewis acid catalyst. These examples fall outside the scope of the instant invention and are presented for comparative purposes only.

EXAMPLE 1

To a 500 milliliter 4-necked flask equipped with a mechanical stirrer, thermometer, and a one-foot long column, filled with glass helices and capped by a distillation head with a thermometer and reflux condenser, are charged 188.2 grams (2.0 moles) of phenol and 4 grams of poly[oxy(dibutylstannylene)] catalyst. This mixture is heated, with stirring, to 180° C. When this temperature is reached 29.5 grams (0.25 mole) of diethyl carbonate are added dropwise from the addition funnel. The addition of the diethyl carbonate is carried out at such a rate so as to maintain the pot temperature at or about 180° C. After the addition of the diethyl carbonate is complete, about one hour, the ethyl alcohol liberated is continuously collected and the quantity collected is noted. The reaction is continued for 7 hours. At the end of the 7 hour reaction period the reaction mixture is weighed and analyzed by gas chromatography for the ethyl phenyl carbonate and the diphenyl carbonate. The results are set forth in Table I.

EXAMPLE 2

The procedure of Example 1 is substantially repeated except that the 4 grams of poly[oxy(dibutylstannylene)] catalyst are replaced with 4 grams of dibutyltin maleate catalyst. The results are set forth in Table I.

EXAMPLE 3

The procedure of Example 1 is substantially repeated except that the 4 grams of poly[oxy(dibutylstannylene)] catalyst are replaced with 4 grams of dibutyltin diacetate catalyst. The results are set forth in Table I.

The following examples illustrate the preparation of aliphatic aromatic (alkyl aryl) carbonates and diaromatic (diaryl) carbonates from dialiphatic (dialkyl) carbonates in accordance with the processes of the instant invention. The catalyst utilized is a physical mixture of a Lewis acid and a protic acid.

EXAMPLE 4

To a 500 milliliter 4-necked flask equipped with a mechanical stirrer, thermommeter, and a one foot long column, filled with glass helices and capped by a distillation head with a thermometer and reflux condenser, are charged 188.2 grams (2.0 moles) of phenol and 4.25 grams of a catalyst system comprised of 4 grams of dibutyltin maleate and 0.25 grams of methanesulfonic acid. This mixture is heated, with stirring, to 180° C. When this temperature is reached 29.5 grams (0.25 mole) of diethyl carbonate are added dropwise from the addition funnel. The addition of the diethyl carbonate is carried out at such a rate so as to maintain the pot temperature at or about 180° C. After the addition of the diethyl carbonate is complete, about one hour, the ethyl alcohol liberated is continuously collected and the quantity collected is noted. The reaction is continued for 7 hours. At the end of this 7 hour reaction period the reaction mixture is weighed and analyzed by gas chromatography for the ethyl phenyl carbonate and the diphenyl carbonate. The results are set forth in Table I.

EXAMPLE 5

The procedure of Example 4 is substantially repeated except that the 4.25 grams of the catalyst system of Example 4 are replaced with 4.5 grams of a catalyst system comprised of 4 grams of dibutyltin maleate and 0.5 grams of methanesulfonic acid. The results are set forth in Table I.

EXAMPLE 6

The procedure of Example 4 is substantially repeated except that the 4.25 grams of the catalyst system of Example 4 are replaced with 4.5 grams of a catalyst system comprised of 4 grams of dibutyltin diacetate and 0.5 grams of methanesulfonic acid. The results are set forth in Table I

EXAMPLE 7

The procedure of Example 4 is substantially repeated except that the 4.25 grams of the catalyst system of Example 4 are replaced with 4.5 grams of a catalyst system comprised of 4 grams of poly[oxy(dibutylstannylene)] and 0.5 grams of $CF_3SO_3H$. The results are set forth in Table I.

TABLE I

| Example No. | Catalyst (gms.) Lewis acid | Catalyst (gms.) Protic acid | Alcohol liberated (gms.) 3 hrs. | Alcohol liberated (gms.) 5 hrs. | Alcohol liberated (gms.) 7 hrs. | alkyl aryl carbonate (mole %) 7 hrs. | diaryl carbonate (mole %) 7 hrs. |
|---|---|---|---|---|---|---|---|
| 1 | 4.0 | 0 | 0 | 8.5 | 10.3 | 4.0 | 4.0 |
| 2 | 4.0 | 0 | 2.3 | 4.4 | 6.6 | 2.7 | 3.3 |
| 3 | 4.0 | 0 | 1.8 | 3.9 | 5.7 | 0.1 | 0.0 |
| 4 | 4.0 | 0.25 | 6.0 | 10.4 | 11.6 | 14.8 | 7.5 |
| 5 | 4.0 | 0.5 | 3.0 | 5.3 | 10.2 | 4.9 | 1.3 |
| 6 | 4.0 | 0.5 | 2.5 | 4.3 | 6.2 | 1.5 | 0.1 |
| 7 | 4.0 | 0.5 | 4.3 | 9.5 | 12.4 | 5.7 | 6.1 |

The data in Table I clearly illustrates that the processes of the instant invention, i.e. those utilizing the catalyst system comprised of a physical mixture of a Lewis acid and a protic acid, are more efficient in producing the aliphatic aromatic carbonates and the diaromatic carbonates from the dialiphatic cabonates than the process utilizing a catalyst comprised of only a Lewis acid. Thus, a comparison of Example 1 with Examples 4 and 7 shows that the processes of the instant invention result in greater amounts of both the aliphatic aromatic carbonates and diaromatic carbonates being formed than does the process falling outside the scope of the instant invention. A comparison of Example 2 with Example 5 shows that the instant process yields a greater amount of the combined diaromatic carbonate and aliphatic aromatic carbonate than does the prior art process which utilizes only the Lewis acid as the catalyst. A comparison of Example 3 with Example 6 shows that the process utilizing the catalyst of the instant invention yields greater amounts of both the diaromatic carbonate and the aliphatic aromatic carbonate than does the process utilizing only the Lewis acid as a catalyst.

Obviously, other modifications and variations of the present invention are possible in light of the above teachings. It is, therefore, to be understood that changes may be made in the particular embodiments of the invention described which are within the full intended scope of the invention as defined by the appended claims.

What is claimed is:

1. An improved process for preparing an aromatic carbonate selected from aliphatic aromatic carbonates represented by the formula

and diaromatic carbonates represented by the formula

which comprises reacting a phenolic compound with a dialiphatic carbonate represented by the formula

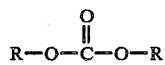

or an aliphatic aromatic carbonate represented by the formula

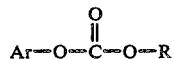

wherein Ar is selected from monovalent aromatic radicals and R is independently selected from monovalent aliphatic radicals in the presence of a catalytic amount of catalyst, the improvement consisting essentially of utilizing as the catalyst a physical admixture consisting essentially of (i) at least one Lewis acid, and (ii) at least one protic acid.

2. The process of claim 1 wherein said catalytic amount is in the range of from about 0.01 to about 25 weight percent, based on the amount of dialiphatic carbonate or aliphatic aromatic carbonate utilized.

3. The process of claim 1 wherein said physical admixture of said Lewis acid and said protic acid contains a weight ratio of said Lewis acid to said protic acid of from about 20:1 to about 1:5.

4. The process of claim 3 wherein said protic acid is selected from inorganic protic acids.

5. The process of claim 4 wherein said inorganic protic acid is selected from HCl, HBr, H$_2$SO$_4$, and H$_3$PO$_4$.

6. The process of claim 3 wherein said protic acid is selected from organic protic acids.

7. The process of claim 6 wherein said organic protic acid is selected from organic sulfonic acids.

8. The process of claim 7 wherein said organic sulfonic acids are selected from alkyl sulfonic acids.

9. The process of claim 7 wherein said organic sulfonic acids are selected from aryl sulfonic acids.

10. The process of claim 6 wherein said organic protic acids are selected from organic phosphonic acids.

* * * * *